United States Patent [19]
Gray et al.

[11] 3,974,087
[45] Aug. 10, 1976

[54] LIQUID CRYSTAL COMPOSITIONS

[75] Inventors: George William Gray, Cottingham; Kenneth John Harrison, Hull; David Sanderson Hulme, Hooton; Edward Peter Raynes, Lower Wick, all of England

[73] Assignee: The Secretary of State for Defence in Her Britannic Majesty's Government of the United Kingdom of Great Britain and Northern Ireland, London, England

[22] Filed: Mar. 15, 1974

[21] Appl. No.: 451,547

[30] Foreign Application Priority Data
Oct. 17, 1973   United Kingdom............... 48468/73

[52] U.S. Cl............................... 252/299; 252/408; 350/150; 350/160 LC
[51] Int. Cl.$^2$...................... C09K 3/34; G02F 1/13
[58] Field of Search...................... 252/408 LC, 299; 350/160 LC

[56] References Cited
UNITED STATES PATENTS
3,891,307   6/1975   Tsukamoto et al........... 350/160 LC FOREIGN PATENTS OR APPLICATIONS
807,165   1/1974   Belgium............................. 252/299
2,024,269   12/1971   Germany............................. 252/299
2,306,738   8/1973   Germany............................. 252/299
2,306,739   8/1973   Germany............................. 252/299

OTHER PUBLICATIONS
Gray, G. W. et al., Electronics Letters, vol. 9, No. 6, pp. 130–131 (Mar. 22, 1973).
Gray, G. W. et al., Electronics Letters, vol. 9, No. 26, pp. 616–617 (Dec. 27, 1973).
Gray, G. W., Molecular Structure and Properties of Liquid Crystals, Academic Press, N.Y., pp. 125–138 (1962).
Gray, G. W. et al., Liquid Crystals & Plastic Crystals, vol. 1, Ellis Horwood, Ltd., Chichester, Eng., pp. 103–174 (Jan. 1974).

*Primary Examiner*—Benjamin R. Padgett
*Assistant Examiner*—T. S. Gron
*Attorney, Agent, or Firm*—Stevens, Davis, Miller & Mosher

[57] ABSTRACT

A range of eutectic mixtures containing at least three compounds having the formula

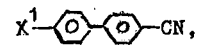

where $X^1$ is an alkyl group, an alkoxy group or a substituted phenyl group

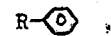

where R is an alkyl or alkoxy group, are described. The eutectic mixtures extend the temperature ranges over which their constituent compounds exhibit liquid crystal properties and are thus useful in liquid crystal devices operating in those temperature ranges.

15 Claims, No Drawings

LIQUID CRYSTAL COMPOSITIONS

The present invention relates generally to liquid crystal materials and devices and particularly to the liquid crystal materials described in U.S. copending application Ser. No. 413247 filed 6th Nov. 1973.

BACKGROUND OF THE INVENTION

In the field of displays there is a requirement for devices having a low power consumption. Devices made from liquid crystal materials have been shown to satisfy this requirement because they have a very large electrical resistance, and at the present time a considerable amount of interest is being shown in such devices for this reason.

There are many known liquid crystal materials; some have been known for many years. Liquid crystal materials are organic materials which exhibit a liquid crystal phase in which the molecules are arranged over limited spatial ranges in an ordered structure.

There are three known kinds of liquid crystal phase. One is known as a smectic mesophase in which the ordering of the molecules is of a lamellar kind. Another is known as a nematic mesophase in which a statistical ordering of the molecules exists parallel to the long axes of the molecules. The third is known as a cholesteric mesophase, in which the ordering of the molecules is of a helical kind.

Liquid crystal materials consist of compounds having a molecular structure which is elongated. For the liquid crystal compounds which have hitherto been used in devices the structure can be generalised and represented as follows:

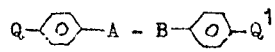

where Q and $Q^1$ are terminal groups and A and B are linkage groups.

Except in the case of certain esters where the unit A-B includes the group CO.O the unit A-B generally includes a double or triple bond. For example the Schiff's bases which are widely used in commercial liquid crystal devices, such as para-methoxy-benzylidene-butylaniline (MBBA) or para-ethoxybenzylidene-butylaniline (EBBA), are compounds containing the unit C=N.

The presence of a double or triple bond in the unit A-B leads to a chemical and/or photochemical instability of the material and is therefore undesirable for this reason. For example, Schiff's bases are readily hydrolysed, even by traces of water, yielding potentially toxic amines.

It had been supposed until recently that the double or triple bond in the unit A-B is desirable to confer rigidity on the molecule and to provide a reasonably high liquid crystal to isotropic liquid transition temperature together with a reasonably low crystalline solid to liquid crystal transition temperature.

Recently, it has been shown that reasonably low crystalline solid to liquid crystal and reasonably high liquid crystal to isotropic liquid transition temperatures can be obtained whilst maintaining low chemical and/or photochemical instability by using as a liquid crystal material one of the materials defined in U.S. copending application Ser. No. 413247. This application describes material consisting of or containing at least one compound having the formula

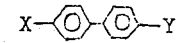

where X and Y are various selected para-substituents.

It is an object of the present invention to increase the temperature ranges over which certain individual compounds having the said formula are liquid crystal.

BRIEF SUMMARY OF THE PRESENT INVENTION

It has now been found that the temperature ranges over which certain individual compounds having the said formula can be significantly increased by mixing at least three of the said compounds together to form a eutectic mixture. Accordingly, the present invention provides a eutectic mixture containing at least three compounds having the formula

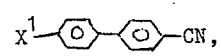

where CN represents a cyano group and where $X^1$ represents a group selected from the following list: an alkyl group, an alkoxy group, or a substituted phenyl group

where R represents an alkyl group or an alkoxy group.

DESCRIPTION OF THE PREFERRED EMBODIMENTS

The following tables describe examples of eutectic mixtures embodying the invention. In the tables the heading M represents the molar percentage of each constituent compound in each mixture, and the headings K — S, S — N, N — I, K — N, K — C and C — I represent respectively the temperature in °C at which the following phase transitions occur for each appropriate mixture: solid to smectic liquid crystal, smectic liquid crystal to nematic liquid crystal, nematic liquid crystal to isotropic liquid, solid to nematic liquid crystal, solid to cholesteric liquid crystal and cholesteric liquid crystal to isotropic liquid. The composition of each constituent compound in each mixture is also represented in the tables. The compositions are all of the kind

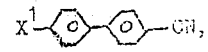

as defined above. Therefore each composition is written in an abbreviated form and is represented by the atoms in its group $X^1$ under the heading $X^1$.

| Mixture 1 | X¹ | M | K—N | N—I |
|---|---|---|---|---|
| | n-$C_5H_{11}$ | 55 | | |
| | n-$C_5H_{11}O$ | 15 | −2 | 54 |
| | n-$C_7H_{15}O$ | 13 | | |
| | n-$C_8H_{17}O$ | 17 | | |

| Mixture 2 | X¹ | M | K—N | N—I |
|---|---|---|---|---|
| | n-$C_7H_{15}$ | 44 | | |
| | n-$C_5H_{11}O$ | 19 | 4 | 61 |
| | n-$C_7H_{15}O$ | 16 | | |
| | n-$C_8H_{17}O$ | 21 | | |

| Mixture 3 | X¹ | M | K—N | N—I |
|---|---|---|---|---|
| | n-$C_7H_{15}$ | 36 | | |
| | n-$C_3H_7O$ | 18 | | |
| | n-$C_5H_{11}O$ | 15 | 0 | 61 |
| | n-$C_7H_{15}O$ | 12 | | |
| | n-$C_8H_{17}O$ | 19 | | |

| Mixture 4 | X¹ | M | K—N | N—I |
|---|---|---|---|---|
| | n-$C_5H_{11}$ | 49 | | |
| | n-$C_3H_7O$ | 15 | | |
| | n-$C_5H_{11}O$ | 12 | −4 | 54 |
| | n-$C_7H_{15}O$ | 10 | | |
| | n-$C_8H_{17}O$ | 14 | | |

| Mixture 5 | X¹ | M | K—N | N—I |
|---|---|---|---|---|
| | n-$C_5H_{11}$ | 32 | | |
| | n-$C_6H_{13}$ | 28 | −18 | 35 |
| | n-$C_7H_{15}$ | 15 | | |
| | n-$C_8H_{17}$ | 25 | | |

| Mixture 6 | X¹ | M | K—N | N—I |
|---|---|---|---|---|
| | n-$C_6H_{13}$ | 49 | | |
| | n-$C_3H_7O$ | 15 | | |
| | n-$C_5H_{11}O$ | 12 | −5 | 49 |
| | n-$C_7H_{15}O$ | 10 | | |
| | n-$C_8H_{17}O$ | 14 | | |

| Mixture 7 | X¹ | M | K—N | N—I |
|---|---|---|---|---|
| | n-$C_5H_{11}$ | 48 | | |
| | n-$C_7H_{15}$ | 29 | −5 | 45 |
| | n-$C_5H_{11}O$ | 12 | | |
| | n-$C_7H_{15}O$ | 11 | | |

| Mixture 8 | X¹ | M | K—N | N—I |
|---|---|---|---|---|
| | n-$C_5H_{11}$ | 53 | | |
| | n-$C_7H_{15}$ | 35 | −1 | 63 |
| | n-$C_5H_{11}$—⌬ | 12 | | |

| Mixture 9 | X¹ | M | K—S | S—N | N—I |
|---|---|---|---|---|---|
| | n-$C_8H_{17}$ | 60 | | | |
| | n-$C_9H_{19}$ | 20 | 5 | 41 | 50 |
| | n-$C_8H_{17}O$ | 20 | | | |

| Mixture 10 | X¹ | M | K—N | N—I |
|---|---|---|---|---|
| | n-$C_7H_{15}$ | 54 | | |
| | n-$C_5H_{11}O$ | 25 | 8 | 55 |
| | n-$C_7H_{15}O$ | 21 | | |

| Mixture 11 | X¹ | M | K—C | C—I |
|---|---|---|---|---|
| | n-$C_5H_{11}O$ | 33 | | |
| | n-$C_7H_{15}O$ | 27 | 12.5 | 48 |
| | $CH_3.CH_2.C^*H.CH_2O$ <br>         \|<br>       $CH_3$ | 40 | | |

| Mixture 12 | $X^1$ | | K—C | C—I |
|---|---|---|---|---|
| | n-$C_5H_{11}$O | 21 | | |
| | n-$C_7H_{15}$O | 17 | 11.5 | 53 |
| | n-$C_8H_{17}$O | 22 | | |
| | $CH_3.CH_2.C^*H.CH_2O$ $CH_3$ | 40 | | |

In Mixtures 11 and 12 the asterisk (*) denotes an optically active carbon atom.

In the above mixtures the molar percentages of the stated constituent compounds may be varied by up to 3% from the stated values without significantly changing the temperature ranges over which the mixtures have their respective mesophases.

The compounds used for which the group $X^1$ represents an n-alkyl group may be prepared by the method described in Example 1 in the said copending patent applications.

The compounds used for which the group $X^1$ represents an alkoxy group may be prepared by the method described in Example 2 in the said copending patent applications.

The compound used for which the group $X^1$ represents a substituted phenyl group may be prepared by the methods described in examples 12 and 13 in the said copending patent applications.

The mixtures may simply be prepared from their constituent compounds by adding the constituent compounds in the appropriate proportions in a small beaker, heating the beaker and its contents until the isotropic liquid phase (a clear liquid) is obtained, stirring the contents of the beaker in that phase for a few minutes and then allowing the beaker and its contents to cool.

The mixtures may be used in one or more of the devices described in the said copending applications.

We claim:
1. A liquid crystal material consisting of an eutectic mixture of at least three compounds having the formula

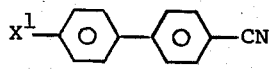

wherein $x^1$ is selected from the group consisting of an alkyl group, an alkoxy group, a substituted phenyl group

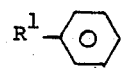

wherein $R^1$ represents an alkyl group, and a substituted phenyl group

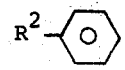

where $R^2$ represents an alkoxy group, the total number of carbon atoms in the alkyl or alkoxy moieties of $X^1$ ranging from 3 to 9.

2. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_5H_{11}$ | 55 |
| n-$C_5H_{11}$O | 15 |
| n-$C_7H_{15}$O | 13 |
| n-$C_8H_{17}$O | 17 |

3. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_7H_{15}$ | 44 |
| n-$C_5H_{11}$O | 19 |
| n-$C_7H_{15}$O | 16 |
| n-$C_8H_{17}$O | 21 |

4. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_7H_{15}$ | 36 |
| n-$C_3H_7$O | 18 |
| n-$C_5H_{11}$O | 15 |
| n-$C_7H_{15}$O | 12 |
| n-$C_8H_{17}$O | 19 |

5. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_5H_{11}$ | 49 |
| n-$C_3H_7$O | 15 |
| n-$C_5H_{11}$O | 12 |
| n-$C_7H_{15}$O | 10 |
| n-$C_8H_{17}$O | 14 |

6. A material as claimed in claim 1 and wherein the material is a mixture of compounds having the following respective groups $X^1$, the compounds being in the following respective molar percentages:

| $X^1$ | Molar percentage (± 3% of compound containing $X^1$ |
|---|---|
| n-$C_5H_{11}$ | 32 |
| n-$C_6H_{13}$ | 28 |
| n-$C_7H_{15}$ | 15 |
| n-$C_8H_{17}$ | 25 |

7. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_6H_{13}$ | 49 |
| n-$C_3H_7O$ | 15 |
| n-$C_5H_{11}O$ | 12 |
| n-$C_7H_{15}O$ | 10 |
| n-$C_8H_{17}O$ | 14 |

8. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_5H_{11}$ | 48 |
| n-$C_7H_{15}$ | 29 |
| n-$C_5H_{11}O$ | 12 |
| n-$C_7H_{15}O$ | 11 |

9. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_5H_{11}$ | 53 |
| n-$C_7H_{15}$ | 35 |
| n-$C_5H_{11}$—⬡— | 12 |

10. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_8H_{17}$ | 60 |
| n-$C_9H_{19}$ | 20 |
| n-$C_8H_{17}O$ | 20 |

11. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_7H_{15}$ | 54 |
| n-$C_5H_{11}O$ | 25 |
| n-$C_7H_{15}O$ | 21 |

12. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_5H_{11}O$ | 33 |
| n-$C_7H_{15}O$ | 27 |
| $CH_3.CH_2.C^*H.CH_2O$ <br>           \|<br>          $CH_3$ | 40 |

13. A material as claimed in claim 1 and wherein the material is a mixture of compounds having the following respective groups $X^1$, the compounds being in the following respective molar percentages:

| $X^1$ | Molar percentage (± 3%) of compound containing $X^1$ |
|---|---|
| n-$C_5H_{11}O$ | 21 |
| n-$C_7H_{15}O$ | 17 |
| n-$C_8H_{17}O$ | 22 |
| $CH_3.CH_2.C^*H.CH_2O$ <br>          \|<br>          $CH_3$ | 40 |

14. A mixture as claimed in claim 1 comprising a cyanoterphenyl and a plurality of cyanobiphenyls.

15. A mixture as claimed in claim 14 wherein said cyanoterphenyl is 4''-pentyl-4'-cyano-p-terphenyl.

* * * * *